(12) United States Patent
Ingalls

(10) Patent No.: US 9,956,119 B2
(45) Date of Patent: May 1, 2018

(54) BULLET EAR PLUG

(71) Applicant: 2 Monkey Trading, LLC, Orlando, FL (US)

(72) Inventor: Doug Ingalls, Orlando, FL (US)

(73) Assignee: 2 Monkey Trading, LLC, Orlando, FL (US)

( * ) Notice: Subject to any disclaimer, the term of this patent is extended or adjusted under 35 U.S.C. 154(b) by 360 days.

(21) Appl. No.: 14/929,481

(22) Filed: Nov. 2, 2015

(65) Prior Publication Data

US 2017/0119584 A1    May 4, 2017

(51) Int. Cl.
*A61F 11/08* (2006.01)

(52) U.S. Cl.
CPC .......... *A61F 11/08* (2013.01); *A61F 2210/00* (2013.01); *A61F 2220/005* (2013.01); *A61F 2230/0006* (2013.01)

(58) Field of Classification Search
CPC ............. A61F 11/08; A61F 2230/0006; A61F 2210/00; A61F 2220/005; A61F 11/06; A61F 2011/085; A61F 11/00; A61F 11/10; A61F 11/12; A61F 11/14; H04R 1/10; H04R 1/1008; H04R 1/1016; A42B 1/06; A42B 1/16
USPC ...... 381/332, 312, 150, 23.1, 322, 328, 151, 381/370, 380; 181/129, 130, 135, 467, 181/464, 466, 128; 128/864, 868, 865, 128/866, 867
See application file for complete search history.

(56) References Cited

U.S. PATENT DOCUMENTS

| | | | |
|---|---|---|---|
| 4,582,053 A * | 4/1986 | Wilson | A61F 11/08 128/867 |
| 4,867,149 A † | 9/1989 | Falco | |
| 4,936,411 A | 6/1990 | Leonard | |
| 5,288,953 A * | 2/1994 | Peart | H04R 1/1016 181/130 |
| 5,449,865 A * | 9/1995 | Desnick | A61B 7/02 181/131 |
| 7,305,992 B2 | 12/2007 | Fleming | |
| D590,055 S † | 4/2009 | Butler | |
| 2007/0183613 A1* | 8/2007 | Juneau | A61F 11/10 381/322 |

(Continued)

OTHER PUBLICATIONS http://www.everydaynodaysoff.com/2009/11/07/using-modified-spent-casings-as-hearing-protection/.†

*Primary Examiner* — Tarla Patel
(74) *Attorney, Agent, or Firm* — Kevin Keener; Keener and Associates

(57) ABSTRACT

A novel earplug is disclosed. The earplug comprises an elastomeric insert and a metal casing. The elastomeric insert is substantially cylindrical in shape and has a first end and a second end. The metal casing is substantially cylindrical in shape and comprises a circular outer wall, an internal cavity disposed within the circular outer wall, and a first end and a second end disposed the opposite end of the first end. The first end has a substantially flat base covering the first end and the second end has an opening into the internal cavity. The first end of the elastomeric insert is disposed through the second end of the metal casing and is secured with an adhesive within the internal cavity of the metal casing. The second end of the elastomeric insert extends outward from the metal casing.

19 Claims, 8 Drawing Sheets

(56) References Cited

U.S. PATENT DOCUMENTS

2010/0198135 A1\* 8/2010 Morriss .................. A61F 11/00
604/21

\* cited by examiner
† cited by third party

BULLET EAR PLUG

FIELD OF THE INVENTION

The invention pertains generally to hearing implements and more particularly a safety ear plug having an elastomer insert surrounded with a metal casing.

BACKGROUND OF INVENTION

Ear plugs are known and used as part of standard personal protection equipment. A user will insert a pair of ear plugs into his ear canals to lessen the amount of sound entering into his ears. Without using ear plugs, a user who is exposed to ongoing high levels of noise can be subject to hearing loss. Standard ear plugs are composed of a compressible foam material. This design is limited in that often the ear plugs are difficult to remove. What is needed is a firm member of the earplug which presents an easy means for removal.

Historically, bullets have been used as ear plugs. Military service members have been known to use rifle bullets as ear plugs both in time of war and in time of peace. Bullets present an easy means for removing them from a user's ears since they are firm and easy to grab. However, the metal ends inserted into the ear canal are uncomfortable to wear. What is needed is an ear plug with a soft elastomeric insert which is comfortable to wear with a metal outer casing presenting an easy means for removal.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The invention is directed toward an earplug comprising an elastomeric insert and a metal casing. The elastomeric insert is substantially cylindrical in shape and has a first end and a second end. The metal casing is substantially cylindrical in shape and comprises a circular outer wall, an internal cavity disposed within the circular outer wall, and a first end and a second end disposed the opposite end of the first end. The first end has a substantially flat base covering the first end and the second end has an opening into the internal cavity. The first end of the elastomeric insert is disposed through the second end of the metal casing and is secured with an adhesive within the internal cavity of the metal casing. The second end of the elastomeric insert extends outward from the metal casing.

In another embodiment, the earplug further comprises one or more flanges disposed laterally from the second end of the elastomeric insert. The earplug may further comprise one or more recesses disposed in the first end of the elastomeric insert. The elastomeric insert may be composed of silicone. In another embodiment, the metal casing further comprises a circular recess disposed in the circular wall and a lip disposed in the circular wall between the circular recess and the first end of the metal casing. In another embodiment, the metal casing further comprises a circular head disposed in the substantially flat base of the first end of the metal casing, the circular head comprising a flat base section and a circular wall extending substantially perpendicular to the flat base section, the circular wall extending into the internal cavity of the metal casing.

The invention is also directed toward a method for applying the earplug to an ear canal of a user comprising grasping the metal casing of the earplug and inserting the elastomeric insert into the ear canal of a user. The method may further comprise grasping the metal casing of the earplug and removing the elastomeric insert from the ear canal of a user.

Still other embodiments of the present invention will become readily apparent to those skilled in this art from the following description wherein there is shown and described the embodiments of this invention, simply by way of illustration of the best modes suited to carry out the invention. As it will be realized, the invention is capable of other different embodiments and its several details are capable of modifications in various obvious aspects all without departing from the scope of the invention. Accordingly, the drawing and descriptions will be regarded as illustrative in nature and not as restrictive.

BRIEF DESCRIPTION OF THE DRAWINGS

Various exemplary embodiments of this invention will be described in detail, wherein like reference numerals refer to identical or similar components, with reference to the following figures, wherein.

DETAILED DESCRIPTION OF THE PREFERRED EMBODIMENT

Figure 1:
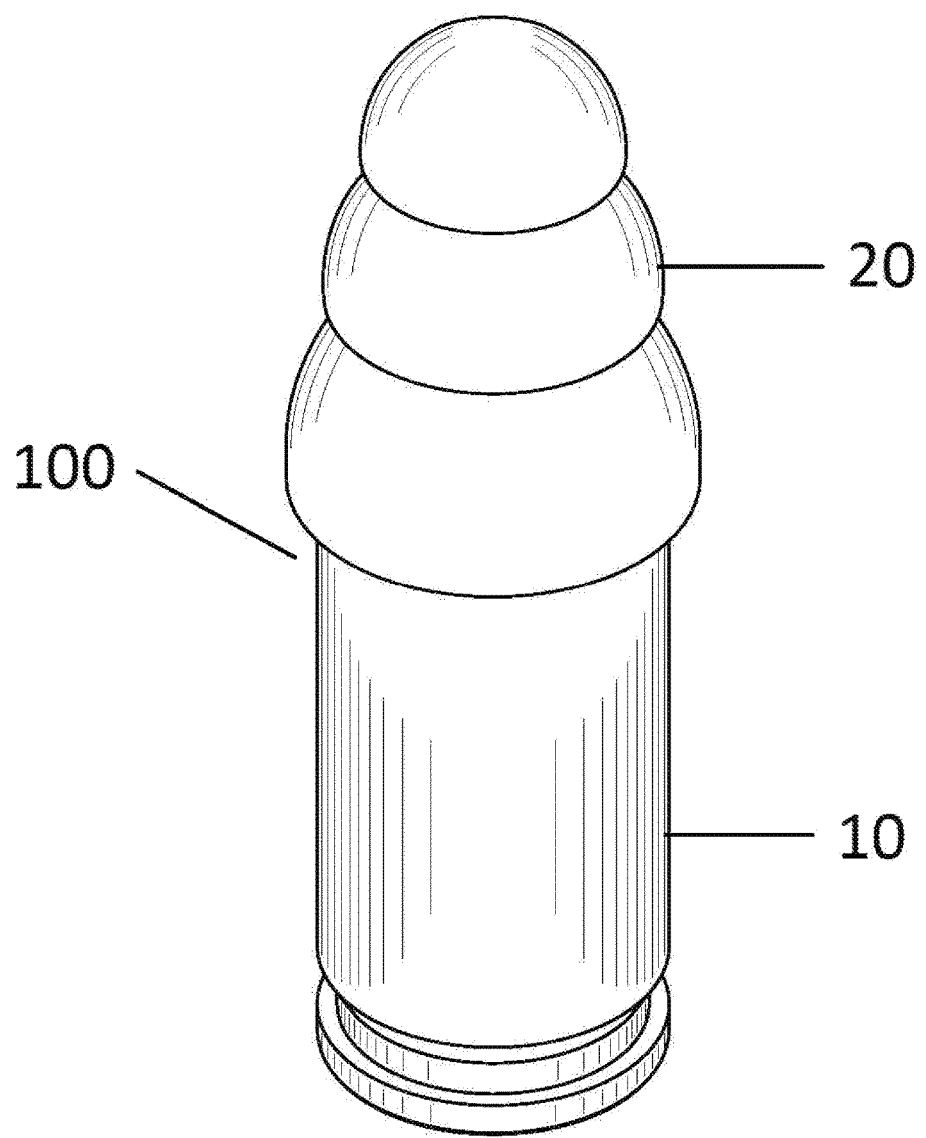
FIG. 1 is a top perspective view of the ear plug.
Figure 2:
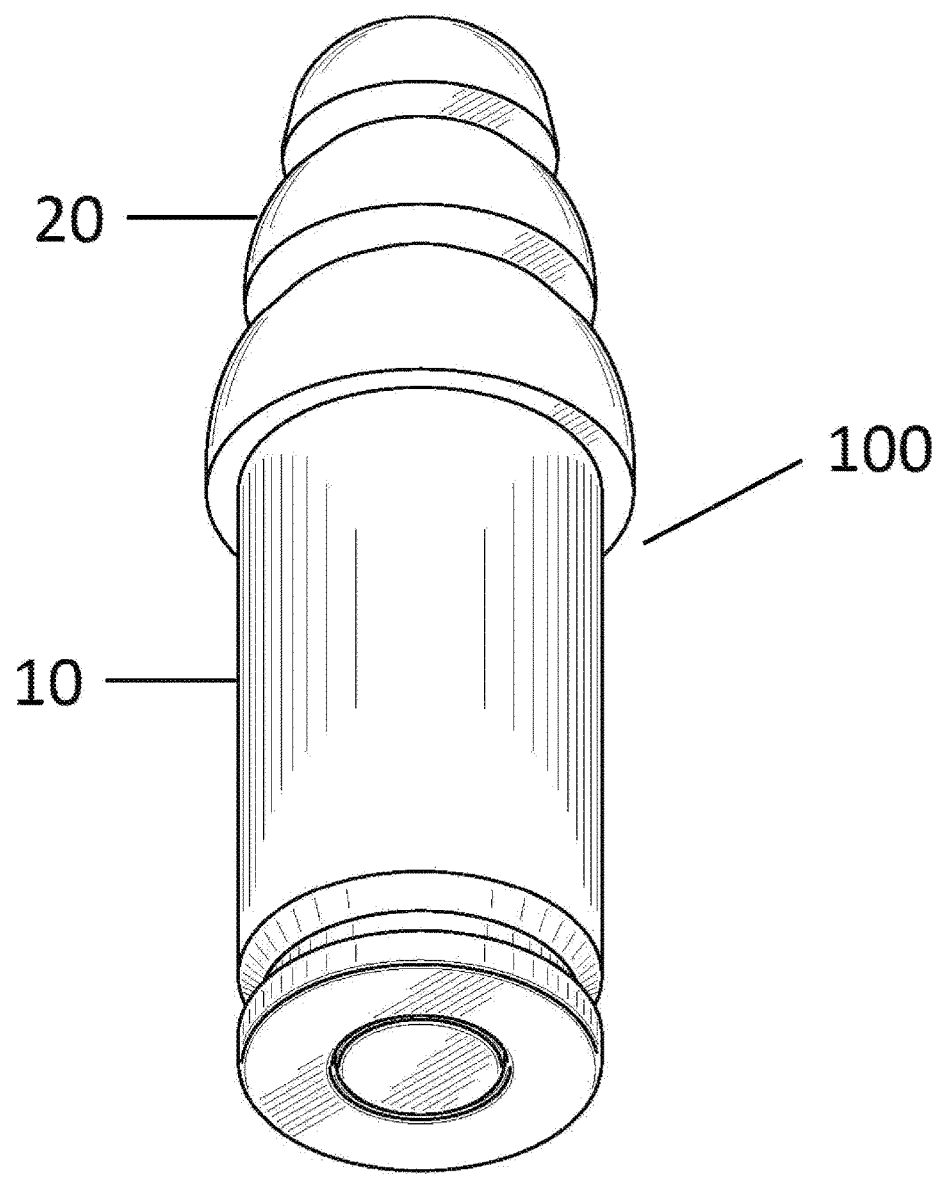
FIG. 2 is a bottom perspective view of the ear plug.
Figure 3:
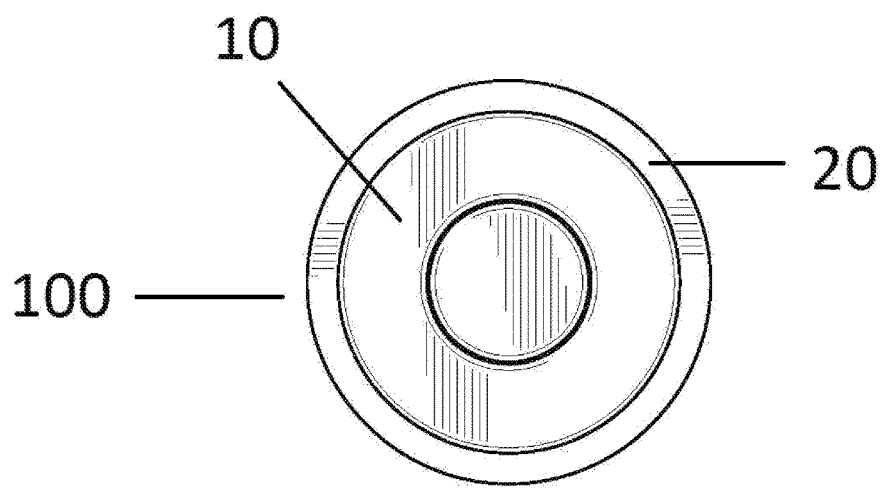
FIG. 3 is a bottom view of the ear plug.
Figure 4:
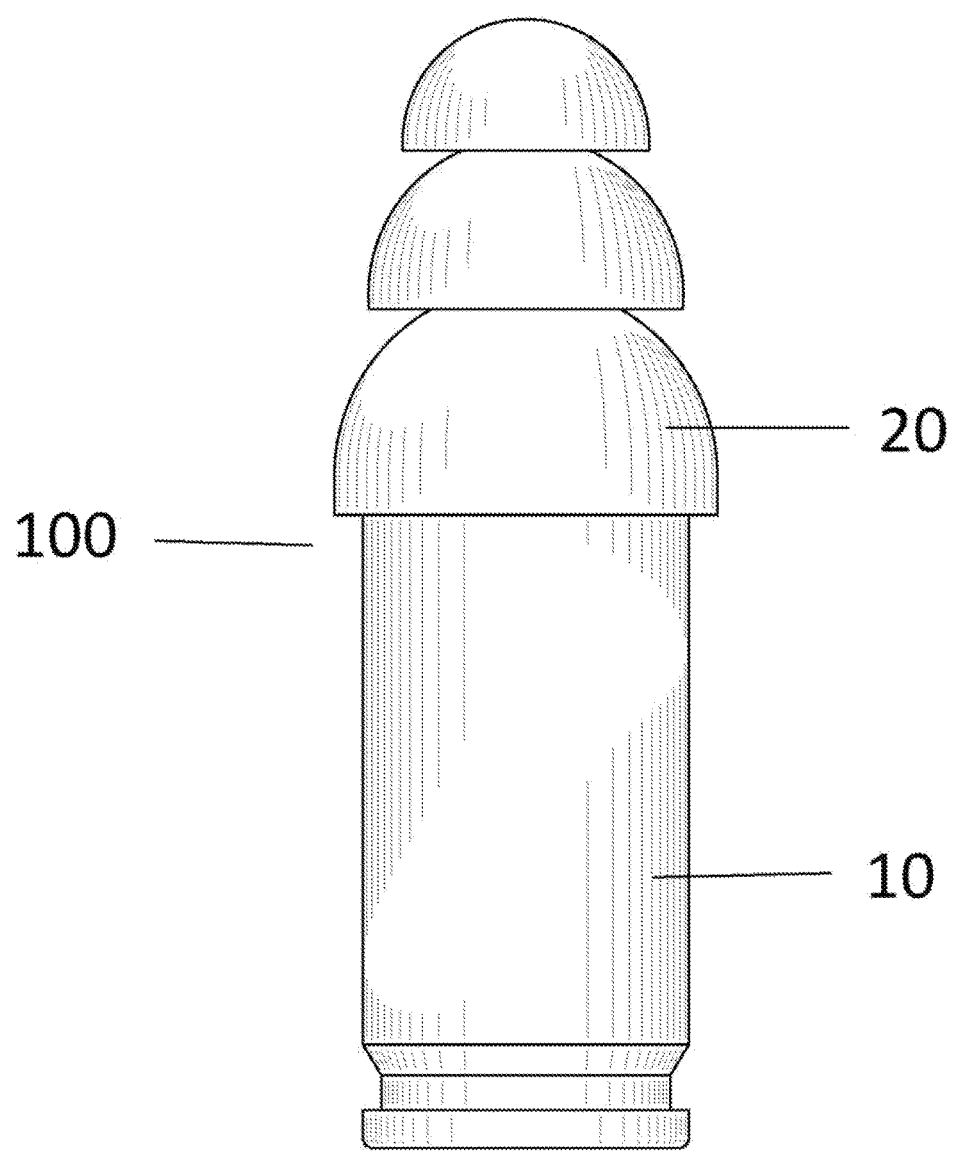
FIG. 4 is a side view of the ear plug.

The claimed subject matter is now described with reference to the drawings. In the following description, for purposes of explanation, numerous specific details are set forth in order to provide a thorough understanding of the claimed subject matter. It may be evident, however, that the claimed subject matter may be practiced with or without any combination of these specific details, without departing from the spirit and scope of this invention and the claims.

Referring to FIG. 1 through FIG. 4 the preferred embodiment of the ear plug 100 is displayed. The ear plug 100 comprises a metal casing 10 and an elastomeric insert 20. The metal casing 100 may be any size, shape, and dimension. In the preferred embodiment the metal casing 10 is cylindrical in shape with a first end and a second end. The metal casing 10 may be made from any type of metal. In the preferred embodiment, the metal casing 10 is an outer casing to a bullet or other type of ammunition casing. The elastomeric insert 20 is a shaped insert fitting configured to fit within the ear canal of a user and prevent sound from entering the user's ear. The elastomeric insert 20 may be any size, shape, and dimension. The elastomeric insert 10 may be made from any type of elastomer. The elastomer may be silicone, rubber, synthetic rubber, plastic, or other compressible compound.

Figure 5:
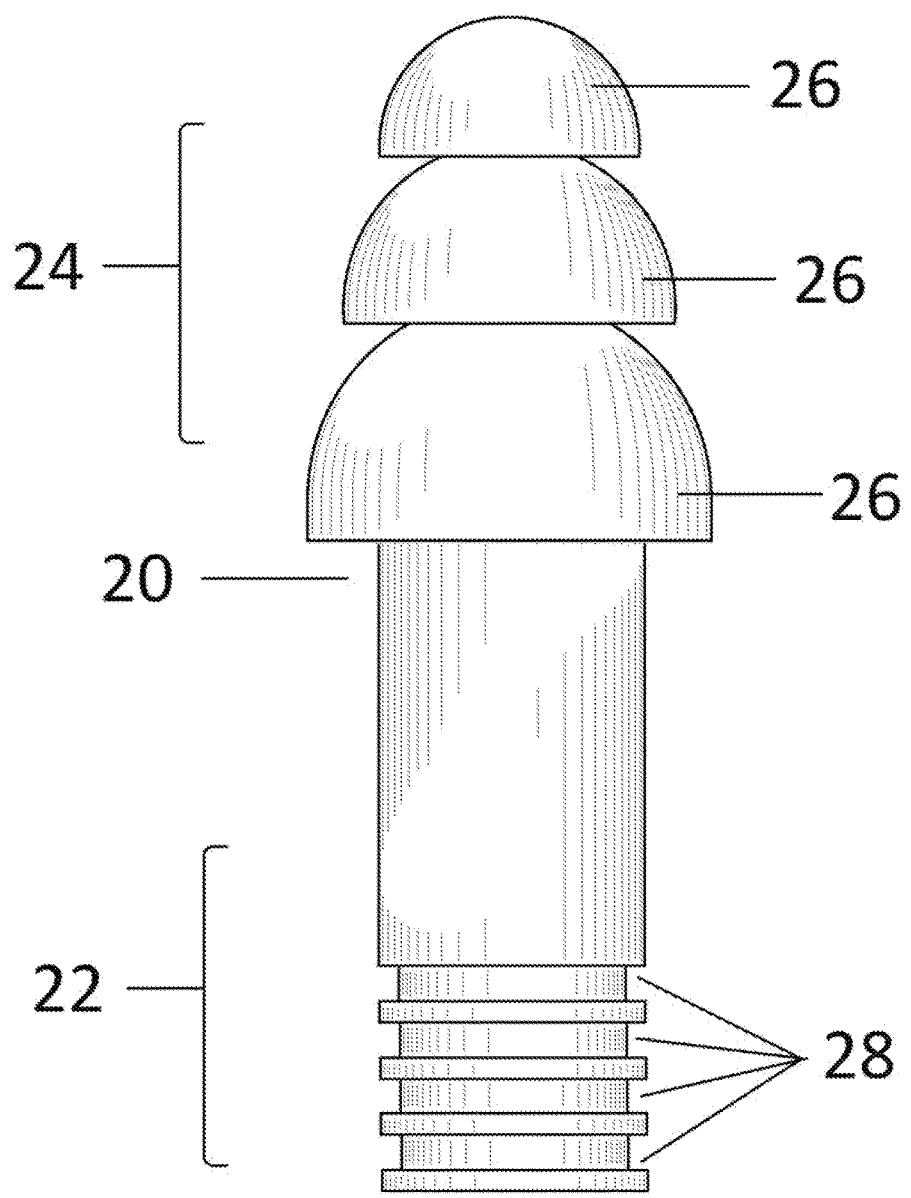
FIG. 5 is a side view of the elastomeric insert for the ear plug.

Referring to FIG. 5, a side view of the elastomeric insert 20 is displayed. The elastomeric insert 20 has a first end 22 and a second end 24. The first end 22 is a cylindrical member extending from the second end 24. The first end 22 is configured to complement the metal casing 10. The second end 24 is a substantially cylindrical and configured to fit within the ear canal of a user. The second end 24 may be any size, shape, and configuration to fit within the ear canal of a user. In the preferred embodiment the second end 24 has a plurality of flanges 26. The flanges 26 are a series of concentric circular protrusions tapering from the first end 22 to the distal portion of the second end 24. The second end 24 may have any number of flanges 26. The diameter of the second end 24 is larger than the diameter of the first end 22. In the preferred embodiment, the diameter of the flanges 26 is larger proximal to the first end 22 and tapers progressively smaller in diameter at the distal end of the second end 24. In the preferred embodiment, the first end 22 has a one or more recesses 28. The one or more recesses 28 may be any size, shape, configuration, position, or depth. In the preferred embodiment the recesses 28 are circular rings which indent into the outer circumference of the first end 22 and are separated by ridges. In other embodiments the recesses 28 are polygonal shapes inset into the first end 22. In another embodiment the second end 24 has no flanges 26 but is a smooth cylindrical member extending from the first end 22. In another embodiment, the first end 22 has no recesses 28 but is a smooth cylindrical member.

Figure 6:
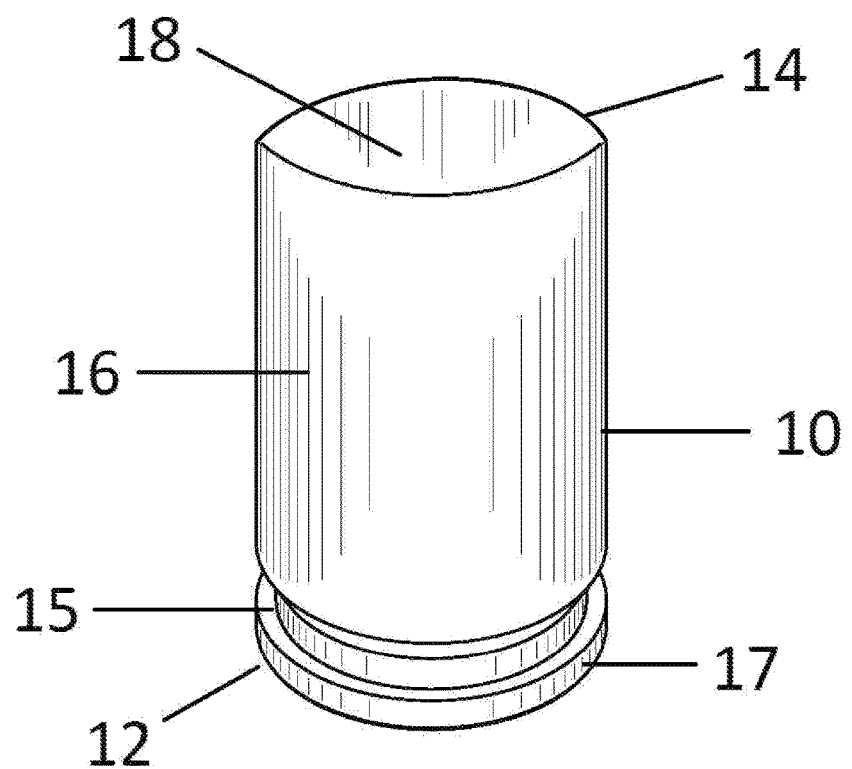
FIG. 6 is a top perspective view of the metal casing of the ear plug.
Figure 7:
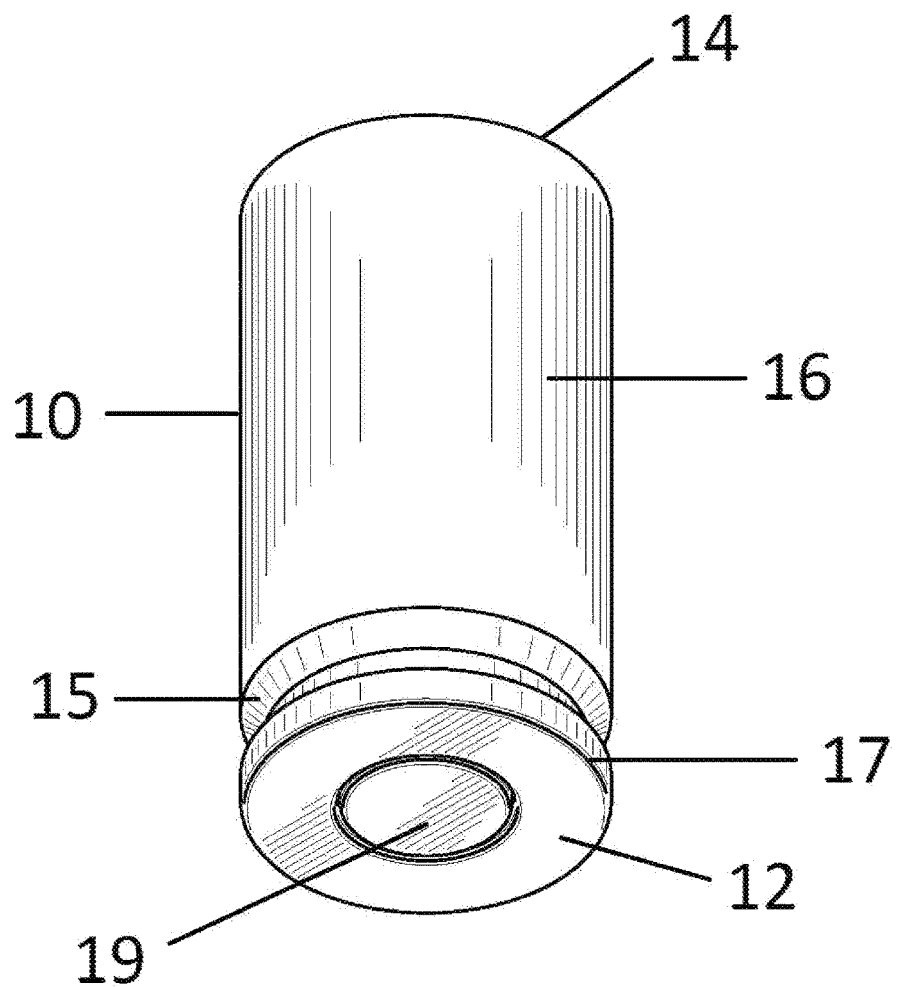
FIG. 7 is a bottom perspective view of the metal casing of the ear plug.

Referring to FIG. 6 and FIG. 7, the preferred embodiment of the metal casing 10 is displayed. The metal casing 10 has a cylindrical wall 16 terminating in a first end 12 and a second end 14. The first end 12 is a substantially flat, circular surface which is coextensive with the cylindrical wall 16. The cylindrical wall 16 defines an internal cavity 18 with an opening at the second end 14. The opening at the second end 14 may be any size and shape. In the preferred embodiment the diameter of the opening at the second end 14 is equal to the diameter of the internal cavity 18. The cylindrical wall 16 may be any size and shape. The cylindrical wall 16 may be a smooth continuous body without interruption. Alternatively, in the preferred embodiment, the cylindrical wall 16 has a circular recess 15 proximate to the first end 12 of the metal casing 10, making gripping of the metal casing 10 easier for the user. Disposed at the first end 12 and beside the circular recess 15 is a lip 17. The lip 17 is a flange projecting radially from the circular wall 16. The lip 17 may be any size and shape. In the preferred embodiment the lip 17 is circular with a diameter equal to the diameter of the circular wall 16.

In one embodiment the first end 12 may be a smooth and flat surface. Alternatively, in the preferred embodiment displayed in FIG. 7, the first end 12 contains a circular head 19, which is reminiscent of a primer cap in a firearm cartridge. In the preferred embodiment, the circular head 19 is a cylindrical shape with side walls extending into the internal cavity 18 of the metal casing 10. In other embodiments the head 19 may be any size and shape.

Figure 8:
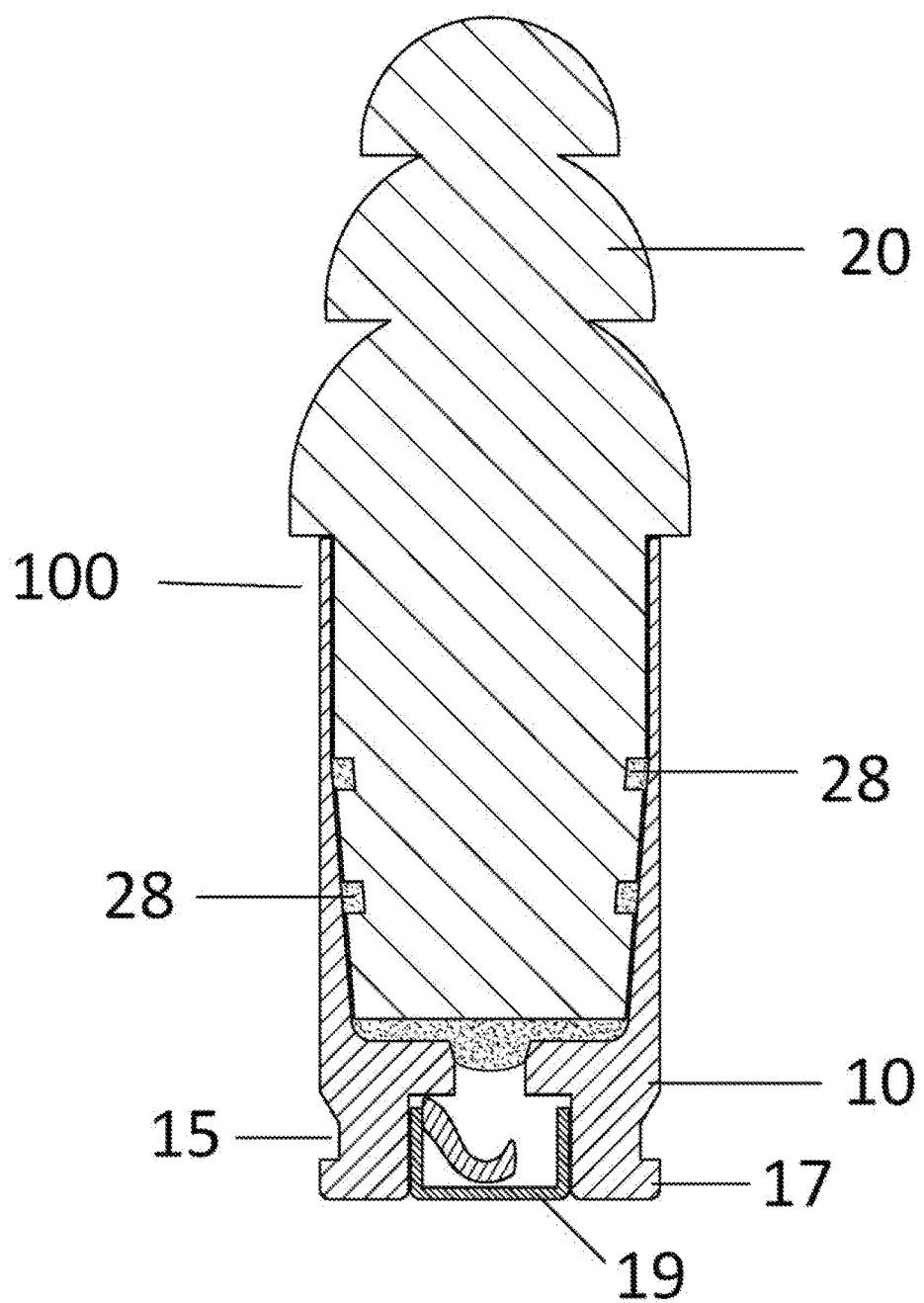
FIG. 8 is a cut away side view of the ear plug.

Referring to FIG. 8, a cutaway view of the ear plug 100 is illustrated. The first end 22 of the elastomeric insert 20 is glued into place within the internal cavity 18 of the metal casing 10. An adhesive is placed within the recesses 28 of the first end 22 and then the first end 22 is inserted into the internal cavity 18 of the metal casing 10. The adhesive then contacts the inner surface of the cylindrical wall 16 and dries. Once dried, the adhesive holds the elastomeric insert 20 in the metal casing 10.

To use the ear plug 100, a user grasps the metal casing 10 and inserts the second end 24 of the elastomeric insert 20 into the user's ear canal. The elastomeric insert 20 substantially fills the ear canal of the user to prevent sound from entering the user's ear. To remove the ear plug 100 the user grasps the metal casing 10, at the circular recess 15 and lip 17, and pulls the elastomeric insert 20 out of the ear canal of the user.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

The invention claimed is:

1. An earplug comprising
   a) an elastomeric insert
      i) said elastomeric insert being substantially cylindrical in shape and having a first end and a second end;
   b) a metal casing
      i) said metal casing being substantially cylindrical in shape and comprising
         (1) a circular outer wall;
         (2) an internal cavity disposed within the circular outer wall;
         (3) a first end and a second end disposed the opposite end of said first end
            (a) wherein said first end has a substantially flat base covering said first end;
            (b) wherein said second end has an opening into said internal cavity wherein said metal casing further comprises a circular recess disposed in said circular wall and a lip disposed in said circular wall between said circular recess and said first end of said metal casing;
   c) wherein said first end of said elastomeric insert is disposed through said second end of said metal casing, said elastomeric insert being secured with an adhesive within said internal cavity of said metal casing;
   d) wherein said second end of said elastomeric insert extends outward from said metal casing.

2. The earplug as in claim 1 further comprising one or more flanges disposed laterally from said second end of said elastomeric insert.

3. The earplug as in claim 2 further comprising one or more recesses disposed in said first end of said elastomeric insert.

4. The earplug as in claim 3 wherein said elastomeric insert is composed of silicone.

5. The earplug as in claim 4 wherein said metal casing further comprises a circular recess disposed in said circular wall and a lip disposed in said circular wall between said circular recess and said first end of said metal casing.

6. The earplug as in claim 5 wherein said metal casing further comprises a circular head disposed in said substantially flat base of said first end of said metal casing, said circular head comprising a flat base section and a circular wall extending substantially perpendicular to said flat base section, said circular wall extending into said internal cavity of said metal casing.

7. The earplug as in claim 3 wherein said metal casing further comprises a circular recess disposed in said circular wall and a lip disposed in said circular wall between said circular recess and said first end of said metal casing.

8. The earplug as in claim 7 wherein said metal casing further comprises a circular head disposed in said substantially flat base of said first end of said metal casing, said circular head comprising a flat base section and a circular wall extending substantially perpendicular to said flat base section, said circular wall extending into said internal cavity of said metal casing.

9. The earplug as in claim 3 wherein said metal casing further comprises a circular head disposed in said substantially flat base of said first end of said metal casing, said circular head comprising a flat base section and a circular wall extending substantially perpendicular to said flat base section, said circular wall extending into said internal cavity of said metal casing.

10. The earplug as in claim 1 further comprising one or more recesses disposed in said first end of said elastomeric insert.

11. The earplug as in claim 10 wherein said metal casing further comprises a circular recess disposed in said circular wall and a lip disposed in said circular wall between said circular recess and said first end of said metal casing.

12. The earplug as in claim 11 wherein said metal casing further comprises a circular head disposed in said substantially flat base of said first end of said metal casing, said circular head comprising a flat base section and a circular wall extending substantially perpendicular to said flat base section, said circular wall extending into said internal cavity of said metal casing.

13. The earplug as in claim 12 wherein said elastomeric insert is composed of silicone.

14. The earplug as in claim 10 wherein said metal casing further comprises a circular head disposed in said substantially flat base of said first end of said metal casing, said circular head comprising a flat base section and a circular wall extending substantially perpendicular to said flat base section, said circular wall extending into said internal cavity of said metal casing.

15. The earplug as in claim 10 wherein said elastomeric insert is composed of silicone.

16. The earplug as in claim 1 wherein said elastomeric insert is composed of silicone.

17. The earplug as in claim 1 wherein said metal casing further comprises a circular head disposed in said substantially flat base of said first end of said metal casing, said circular head comprising a flat base section and a circular wall extending substantially perpendicular to said flat base section, said circular wall extending into said internal cavity of said metal casing.

18. A method for applying an earplug to an ear canal of a user
   a) wherein said earplug comprises
      i) an elastomeric insert
         (1) said elastomeric insert being substantially cylindrical in shape and having a first end and a second end;
      ii) a metal casing
         (1) said metal casing being substantially cylindrical in shape and comprising
            (a) a circular outer wall;
            (b) an internal cavity disposed within the circular outer wall;
            (c) a first end and a second end disposed the opposite end of said first end
               (i) wherein said first end has a substantially flat base covering said first end;
               (ii) wherein said second end has an opening into said internal cavity wherein said metal casing further comprises a circular recess disposed in said circular wall and a lip disposed in said circular wall between said circular recess and said first end of said metal casing;
      iii) wherein said first end of said elastomeric insert is disposed through said second end of said metal casing, said elastomeric insert being secured with an adhesive within said internal cavity of said metal casing;
      iv) wherein said second end of said elastomeric insert extends outward from said metal casing;
   b) said method comprising grasping said metal casing of said earplug and inserting said elastomeric insert into the ear canal of a user.

19. The method as in claim 18 further comprising grasping said metal casing of said earplug and removing said elastomeric insert from the ear canal of a user.

\* \* \* \* \*